(12) United States Patent
Gharda

(10) Patent No.: US 9,029,564 B2
(45) Date of Patent: May 12, 2015

(54) PROCESS FOR SYNTHESIS OF FIPRONIL

(76) Inventor: Keki Hormusji Gharda, Mumbai (IN)

( * ) Notice: Subject to any disclaimer, the term of this patent is extended or adjusted under 35 U.S.C. 154(b) by 51 days.

(21) Appl. No.: 14/122,721

(22) PCT Filed: Dec. 15, 2011

(86) PCT No.: PCT/IN2011/000858
§ 371 (c)(1),
(2), (4) Date: Feb. 18, 2014

(87) PCT Pub. No.: WO2012/164571
PCT Pub. Date: Dec. 6, 2012

(65) Prior Publication Data
US 2014/0194630 A1 Jul. 10, 2014

(30) Foreign Application Priority Data
May 30, 2011 (IN) .......................... 1589/MUM/2011

(51) Int. Cl.
*C07D 231/44* (2006.01)
(52) U.S. Cl.
CPC .................................... *C07D 231/44* (2013.01)
(58) Field of Classification Search
None
See application file for complete search history.

(56) References Cited

U.S. PATENT DOCUMENTS

2009/0030211 A1  1/2009  Gharda et al.

FOREIGN PATENT DOCUMENTS

| CN | 101250158 | 12/2011 |
| EP | 0295117 | 12/1988 |
| IN | 183/MUM/2010 | 11/2012 |
| WO | 01/30760 | 5/2001 |
| WO | 2007/122440 | 11/2007 |
| WO | 2009/077853 | 6/2009 |

OTHER PUBLICATIONS

International Search Report issued in corresponding International Application No. PCT/IN2011/000858 on May 31, 2012.

*Primary Examiner* — Kamal Saeed
(74) *Attorney, Agent, or Firm* — Whiteford, Taylor & Preston, LLP; Gregory M. Stone

(57) ABSTRACT

A process for preparation of Fipronil (i.e. 5-amino-1-(2,6-dichloro-4-trifluoromethylphenyl)-3-cyano-4-trifluoro-methylsulphinyl-pyrazole) is provided, which comprises oxidizing 5-amino-1-(2,6-dichloro-4-trifluoromethylphenyl)-3-cyano-4-tri-fluoromethylthio-pyrazole with sulfuric acid and hydrogen peroxide as oxidizing agent in the presence of a solvent such as ethylene dichloride, chlorobenzene.

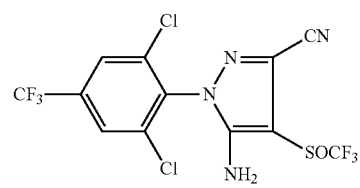

[I]

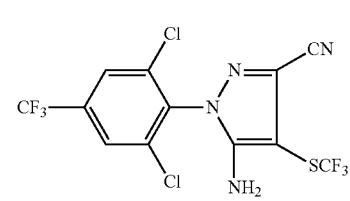

[II]

5 Claims, No Drawings

PROCESS FOR SYNTHESIS OF FIPRONIL

CROSS-REFERENCE TO RELATED APPLICATIONS

This application is a National Stage Entry of PCT/IN2011/000858, filed Dec. 15, 2011, which claims priority to Indian Patent Application No. 1589/MUM/2011, filed May 30, 2011.

BACKGROUND

1. Filed of Invention

The present disclosure relates to a process for preparing 5-amino-1-(2,6-dichloro-4-trifluoromethylphenyl)-3-cyano-4-trifluoromethylsulphinyl pyrazole (Fipronil).

2. Discussion of Related Art

5-Amino-1-(2,6-dichloro-4-trifluoromethylphenyl)-3-cyano-4-trifluoromethyl sulphinyl pyrazole [Fipronil] is one of the important fluorine bearing 1-Aryl pyrazole derivatives developed in the recent two decades. It is a novel pesticide characterized by high efficiency, low toxicity and especially low residue. Commercially fipronil is synthesized by oxidation of thiopyrazole with oxidizing agents in presence of suitable solvents. The process makes use of corrosive and expensive chemicals such as trifluoroacetic acid/hydrogen peroxide, m-chloroperbenzoic acid/dichloromethane/chloroform and the like.

EP 295117 discloses preparation of 5-amino-1-(2,6-dichloro-4-trifluoro methyl phenyl)-3-cyano-4-trifluoromethyl sulphinyl pyrazole by oxidation of 5-amino-1(2,6-dichloro-4-trifluoromethylphenyl)-3-cyano-4-trifluoromethyl-thiopyrazole with meta-chloroperbenzoic acid. A problem encountered in the preparation is the co-formation of the corresponding sulfone compound 5-amino-1-(2,6-dichloro-4-trifluoromethylphenyl)-3-cyano-4-trifluoromethylsulfonyl pyrazole, which is difficult to remove from the sulfoxide.

It has been found that a mixture of trifluoroaceticacid and hydrogen peroxide (trifluoroperaceticacid) gives excellent results in terms of both selectivity and yield. However, the problem associated with the use of trifluoroacetic acid and hydrogen peroxide mixture on large scale is that it leads to corrosion of the glass linings of industrial reaction vessels. This corrosion occurs as a result of the formation of hydrogen fluoride and it prohibits the use of this reagent mixture in such vessels. Further, it was found that the addition of a corrosion inhibiting compound such as boric acid to the reaction mixture inhibits the corrosion process and reduces the speed of corrosion to a level that is typically less than 5 μm/year.

WO01/30760 describes oxidation of 5-amino-1-(2,6-dichloro-4-trifluoromethylphenyl)-3-cyano-4-trifluoromethyl thio-pyrazole with trifluoro-acetic acid (TFA) and hydrogen peroxide in presence of boric acid. Boric acid is used to prevent the corrosion of glass/metal equipment. Whilst this may be effective during oxidation, however TFA is a costly chemical and must be recovered due to process economics.

US20090030211 discloses a process for the preparation of fipronil. The process involves oxidizing 5-amino-3-cyano-1-(2,6-dichloro-4-trifluro methylphenyl)-4-trifluromethylthio pyrazole in a medium comprising an oxidizing agent, trichloroaceticacid and a melting point depressant. The melting point depressant employed in the process is monochloroaceticacid, dichloroaceticacid, methylenedichloride, ethylenedichloride, monochlorobenzene and haloalkane. The process utilizes trichloroacetic acid as a substitute solvent for TFA (trifluoroaceticacid) along with melting point depressant.

IN183/MUM/2010 discloses a process for the preparation of fipronil which obviates the use of large quantity of TFA. The process utilizes a mixture of solvents which provides selective degree of oxidation as that of trifluoroaceticacid along with a oxidant and a corrosive inhibiting agent. The solvent system used is a mixture of trifluoroaceticacid and chlorobenzene in a ratio of 60:40% w/w to 55:45% w/w.

CN101250158 discloses a process for the synthesis of fipronil by oxidation of 5-amino-3-cyano-1-(2,6-dichloro-4-trifluromethylphenyl)-4-trifluromethylthio pyrazole in presence of a phase transfer catalyst selected from the group consisting of tetrabutyl ammonium chloride, tetrabutyl ammonium bromide, 4-N, N-dimethyl pyridine, triethylbenzylammonium chloride, sodium dodecyl sulphonate and trimethyl dodecyl ammonium chloride, in a solvent and sulphuric acid medium.

However, the process disclosed in CN101250158 is expensive process as it utilizes phase transfer catalyst. Further, the process disclosed in CN101250158 involves dissolution of the oxidant in sulphuric acid which causes degradation of oxidant and leads to incomplete oxidation. The process therefore shows inconsistency in the yield and the quality.

Therefore, there is felt a need to develop a simple and in-expensive method for the synthesis of fipronil which overcomes the drawbacks associated with aforesaid process.

SUMMARY OF THE INVENTION

Some of the objects of the invention are as follows:
- To provide a simple process for the preparation of 5-Amino-1-(2,6-dichloro-4-trifluoromethylphenyl)-3-cyano-4-trifluoromethylsulphinyl pyrazole which gives consistent yield and quality.
- To provide a process for the preparation of 5-amino-1-(2,6-dichloro-4-trifluoromethylphenyl)-3-cyano-4-trifluoromethylsulphinylpyrazole which obviates the use of a phase transfer catalyst.
- To provide a process for the preparation of 5-amino-1-(2,6-dichloro-4-trifluoromethylphenyl)-3-cyano-4-trifluoromethylsulphinylpyrazole which is safe, convenient, easy to operate on commercial scale and cost-effective.

In accordance with the present invention, there is provided a process for preparing fipronil, said process comprising the following steps:
a. oxidizing, in a solvent selected from the group consisting of ethylene dichloride, methylene dichloride, carbon tetrachloride, chloroform, dibromoethane, bromobenzene, chlorobenzene and ortho-dichlorobenzene, a reactant mixture containing a compound 5-amino-1-(2,6-dichloro-4-trifluoromethylphenyl)-3-cyano-4-trifluoromethylthio-pyrazole of formula II and concentrated sulfuric acid having concentration in the range of 75% to 98% w/w, with hydrogen peroxide having concentration in the range 40 to 70% w/w, at a temperature in the range of −10° C. to 40° C. to obtain an oxidized product mixture;
b. quenching said product mixture with water at a temperature in the range of 10 to 25° C.;
c. heating the quenched product mixture at a temperature in the range of 60 to 70° C. to obtain a biphasic system containing an aqueous phase containing sulphuric acid and an organic phase containing the oxidized product;
d. isolating said organic phase by separating the aqueous phase;

e. neutralizing the isolated organic phase containing the oxidized product to obtain crude fipronil; and f. crystallizing the crude fipronil to obtain crystallized fipronil.

Typically, the amount of the hydrogen peroxide used is in the range of 0.9 moles to 1.6 moles per mole of the compound II.

Typically, the amount of the solvent used is 100 to 7000 ml per mole of the compound II.

Typically, the amount of the concentrated sulphuric used is 400 gm to 3000 gms per mole of the compound II.

In a preferred embodiment of the present invention the aqueous phase obtained after separation of the organic phase in step (d) is concentrated to obtain concentrated sulphuric acid having concentration in the range of 75% to 85% w/w.

DETAILED DESCRIPTION OF THE INVENTION

The present invention provides a process for the preparation of a compound of formula (I) 5-Amino-1-(2,6-dichloro-4-trifluoromethylphenyl)-3-cyano-4-tri fluoromethylsulphinylpyrazole (Fipronil) by oxidizing a compound 5-amino-1-(2,6-dichloro-4-trifluoromethylphenyl)-3-cyano-4-trifluoromethylthio pyrazole of formula (II)

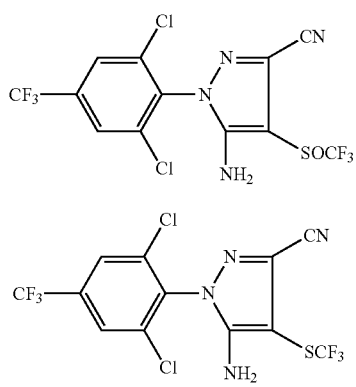

The process for the preparation of fipronil in accordance with the present invention includes the following steps:

preparing a mixture containing a compound 5-amino-1-(2,6-dichloro-4-trifluoromethylphenyl)-3-cyano-4-trifluoro methyl thio-pyrazole and a solvent, cooling the mixture to a temperature in the range of −10 to 20° C. and adding a mineral acid over a period of about 3 to about 4 hours to obtain a reactant mixture, adding an oxidizing agent to the reactant mixture maintaining the temperature in the range of −10 to 20° C., maintaining the reaction at the temperature in the range of 10° C. to 50° C. for a period of 1 to 8 hours to obtain an oxidized product mixture, quenching the product mixture by slowly adding the mixture to chilled water over a period of about 2 hours, heating the quenched mixture at a temperature of about 60 to 70° C. to obtain a biphasic system containing an aqueous phase and an organic phase containing the oxidized product, isolating said organic phase by separating the aqueous phase, neutralizing the isolated organic phase containing the oxidized product to obtain crude fipronil, and crystallizing the crude fipronil to obtain crystallized fipronil.

The oxidant can be added simultaneously along with the mineral acid, however care is taken that the oxidant is not added into sulphuric acid as it will degrade the oxidant.

The mineral acid is concentrated sulphuric acid ($H_2SO_4$) having concentration in the range of of 75% to 98% w/w. The amount of sulphuric acid ($H_2SO_4$) quantity used is in the range of 400 gm to 3000 gm per mole of compound II.

The oxidizing agent is a peroxide compound selected from the group consisting of hydrogen peroxide, t-butyl hydrogen peroxide, benzoyl peroxide and sodium peroxide. Preferably, the oxidizing agent is hydrogen peroxide ($H_2O_2$) having concentration in the range of 40 to 70% w/w.

In accordance with one of the embodiments of the present invention the amount of hydrogen peroxide is in the range of 0.9 moles to 1.6 moles per mole of the compound of formula II.

The solvent is at least one selected from the group consisting of ethylene dichloride, methylene dichloride, carbon tetrachloride, chloroform, dibromoethane, bromobenzene, chlorobenzene and ortho dichlorobenzene. Preferably 100 ml to about 7000 ml of the solvent per mole of the compound of formula II is used in the process.

The following examples are merely illustrative of the invention and should not be construed as limiting.

Example 1

1.5 liter of ethylene dichloride & 421.0 gms of 5-amino-3-cyano-1-(2,6-dichloro-4-trifluromethylphenyl)-4-triflurom-ethylthio pyrazole was charged in a reactor flask with overhead stirring & condenser system. This mass was then cooled to 12-15° C. and 68.0 gms of $H_2O_2$ (50.0% w/w) & 500.0 gms of $H_2SO_4$ (90.0% w/w) were simultaneously added over a period of 3.0 to 4.0 hours. The reaction temperature was then raised to 28-30° C. & maintained for about 2.0 hours. The reaction mass obtained thereafter was slowly added into 1700 ml of chilled water at 10-20° C. over a period of 2.0 hours. To this mass, 1500 ml of ethylene dichloride was added and the mixture was heated to 60° C. in order to separate the aqueous and organic layers. The obtained organic phase was washed with water & then with 5% $NaHCO_3$ solution followed by water wash, till a neutral pH was obtained. The crude yield of fipronil after removal of solvent was 425.0 gms. The crude fipronil was crystallized from same solvent after partial evaporation to yield 325 gms of crystalline fipronil with 94.0% purity.

Example 2

1.5 liter of methylene dichloride & 421.0 gms of 5-amino-3-cyano-1-(2,6-dichloro-4-trifluromethylphenyl)-4-trifluromethylthio pyrazole was charged in a reactor flask with overhead stirring & condenser system. This mass was cooled to 12-15° C. and 68.0 gms of $H_2O_2$ (50.0% w/w) & 500.0 gms of $H_2SO_4$ (90.0% w/w) were simultaneously added to the mass over a period of 3.0-4.0 hours. The reaction temperature was then raised to 28-30° C. & maintained for about 2.0 hours. The reaction mass obtained thereafter was slowly added into 1700 ml of chilled water at a temperature of about 10-20° C. over a period of 2.0 hours. To this mass, 1500 ml of methylene dichloride was added and the mixture was heated to 60° C. to separate the aqueous and organic layers. The organic phase was washed with water & then with 5% $NaHCO_3$ solution, followed by water wash, till a neutral pH was obtained. The crude yield obtained was 425.0 gms. The obtained crude fipronil was then crystallized from same solvent after partial evaporation to yield crystalline Fipronil (325 gms) with 94.0% purity.

Example 3

3.0 liter of ethylene dichloride & 421.0 gms of 5-amino-3-cyano-1-(2,6-dichloro-4-trifluromethylphenyl)-4-trifluromethylthio pyrazole was charged in a reactor flask with overhead stirring & condenser system. This mass was cooled to a temperature of about 5-10° C. 95.0 gms of $H_2O_2$ (50.0% w/w) & 2000.0 gms $H_2SO_4$ (85.0% w/w) were simultaneously added over a period of 3-4 hours. The reaction temperature was maintained at 12-15° C. for about 2.0 hours with monitoring of reaction conversion. The reaction mass obtained thereafter was slowly added into 800 ml of chilled water at a temperature of about 10-20° C. over a period of 2.0 hours. This mass was heated to a temperature of about 60-65° C. to separate the aqueous and organic layers. The organic phase was washed with water & then with 5% $NaHCO_3$, followed by water wash, till a neutral pH was obtained. The crude yield of fipronil after removal of solvent was 435.0 gms. The crude fipronil was then crystallized to yield 350.0 gms of fipronil with 95.50% purity.

Example 4

3.0 liter of ethylene dichloride solvent & 421.0 gms of 5-amino-3-cyano-1-(2,6-dichloro-4-trifluromethylphenyl)-4-trifluromethylthio pyrazole was charged in a reactor flask with overhead stirring & condenser system. This mass was cooled to a temperature of about 5-10° C. and 2500.0 gms of $H_2SO_4$ (85.0% w/w) was added over a period of 3.0 to 4.0 hours. After that, 95.0 gms of $H_2O_2$ (50.0% w/w) was added to the aforesaid mass over a period of 3.0 hours at 11-13° C. The reaction temperature was maintained at a temperature of about 12-15° C. for about 2.0 hours with monitoring of reaction conversion. The reaction mass obtained thereafter was slowly added into 1250 ml of chilled water at a 10-20° C. over a period of 2.0 hours. This mass was heated to a temperature of about 60-65° C. to separate the aqueous and organic layers. The organic phase was washed with water & then with 5% $NaHCO_3$ solution, followed by water wash, till a neutral pH was obtained. The crude yield was 436.0 gms. The crude fipronil was then crystallized from same solvent after partial evaporation to yield 358.0 gms crystalline fipronil of 95.0% purity.

Example 5

3.0 liter of ethylene dichloride solvent & 421.0 gms of 5-amino-3-cyano-1-(2,6-dichloro-4-trifluromethylphenyl)-4-trifluromethylthio pyrazole was charged into a reactor flask with overhead stirring & condenser system. This mass was cooled to a temperature of about 5-10° C. and 1000.0 gms of $H_2SO_4$ (85.0% w/w) was added over a period of 1.5 to 2.0 hours. 61.0 gms of $H_2O_2$ (50.0% w/w) was then added to the aforesaid mass over a period of 3.0 hours at 07-13° C. The reaction temperature was maintained at a temperature of about 10-13° C. for about 1.0 hours. The reaction mass obtained thereafter was slowly added into 370 ml of chilled water at a 10-25° C. over a period of 2.0 hours. This mass was treated as in above experiments to yield crystalline fipronil (315.0 gms) of 95.0-96.5% purity.

Example 6

In a reactor flask with overhead stirring system, 2500 gms of 85.0% W/W $H_2SO_4$ & 100 ml of ethylene dichloride solvent was charged. This mass was cooled under stirring to 3.0-5.0° C. and then 421.0 gms of 5-amino-3-cyano-1-(2,6-dichloro-4-trifluromethylphenyl)-4-trifluromethylthio pyrazole solid was added over a period 1.0 hour. 95.0 gms of $H_2O_2$ (50.0% w/w) was then added to the aforesaid mass over a period of 3.0 hours at 3-8° C. The reaction temperature was maintained at a temperature of about 6-13° C. for about 3.0 hours. The reaction mass obtained thereafter was slowly added into 475-500 ml of chilled water at a 10-25° C. over a period of 2.0 hours. This mass was filtered/centifuged at 30-35° C. and the solid cake was washed with plenty of water to make it free of acidity. The crude cake was dried and then crystallized in 1000 ml of dichloro ethane solvent to yield 360.0 gms of crystalline fipronil with 94.0-96.0% purity.

Example 7

The aqueous layer was collected from example No. 5, it contained 62% W/W $H_2SO_4$. The aqueous layer was extracted with 200 ml ethylene dichloride solvent to remove dissolved impurities, if any. The extracted aqueous sulphuric acid was then concentrated under reduced pressure of 10-15 mmHg and at 120-130° C. temperature to yield 900 grams of concentrated sulphuric acid having strength of 85-87% W/W.

Oxidation of 5-amino-3-cyano-1-(2,6-dichloro-4-trifluromethylphenyl)-4-trifluromethyl thio pyrazole (378 gms) was carried out using concentrated sulpuric acid (85-87% W/W) as obtained above in similar manner as described in example No. 5 to yield crystalline fipronil (280 gms) of 95.0-96.5% purity.

Technical Advancement and Economic Significance:

The process of the present invention obviates the use of a phase transfer catalyst.

The process of the present invention prevents degradation of oxidant by avoiding a step of dissolution of oxidant in sulphuric acid.

The crude yield of the product (fipronil) is between 97-99%.

The spent $H_2SO_4$ of 60-70% W/W generated in the process will be recyclable after concentrating back to 85-86% W/W.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary.

While considerable emphasis has been placed herein on the specific steps of the preferred process, it will be appreciated that additional steps can be made and that many changes can be made in the preferred steps without departing from the principles of the invention. These and other changes in the preferred steps of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A process for preparing fipronil, said process comprising the following steps:
   a. oxidizing, in a solvent selected from the group consisting of ethylene dichloride, methylene dichloride, carbon tetrachloride, chloroform, dibromoethane, bromobenzene, chlorobenzene and ortho-dichlorobenzene, a reactant mixture containing a compound 5-amino-1-(2,6-dichloro-4-trifluoromethylphenyl)-3-cyano-4-trifluoro methyl thio-pyrazole of formula II

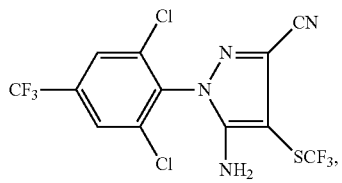

and concentrated sulfuric acid having concentration in the range of 75% to 98% w/w, with hydrogen peroxide having concentration in the range 40 to 70% w/w, at a temperature in the range of −10° C. to 40° C. to obtain an oxidized product mixture;

b. quenching said product mixture with water at a temperature in the range of 10 to 25° C.;

c. heating the quenched product mixture at a temperature in the range of 60 to 70° C. to obtain a biphasic system containing an aqueous phase containing sulphuric acid and an organic phase containing the oxidized product;

d. isolating said organic phase by separating the aqueous phase;

e. neutralizing the isolated organic phase containing the oxidized product to obtain crude fipronil; and f. crystallizing the crude fipronil to obtain crystallized fipronil.

2. The process as claimed in claim 1, wherein the amount of the hydrogen peroxide used is in the range of 0.9 moles to 1.6 moles per mole of the compound of Formula II.

3. The process as claimed in claim 1, wherein the amount of the solvent used is 100 to 7000 ml per mole of the compound of Formula II.

4. The process as claimed in claim 1, wherein the amount of the concentrated sulphuric used is 400 gm to 3000 gms per mole of the compound of Formula II.

5. The process as claimed in claim 1, wherein the aqueous phase obtained after separation of the organic phase in step (d) is concentrated to obtain concentrated sulphuric acid having concentration in the range of 75% to 85% w/w.

* * * * *